(12) United States Patent
Fujioka et al.

(10) Patent No.: US 6,423,046 B1
(45) Date of Patent: Jul. 23, 2002

(54) ABSORBENT ARTICLE

(75) Inventors: Yoshihisa Fujioka; Yoshio Ono; Katsumi Mizutani, all of Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 09/450,326

(22) Filed: Nov. 29, 1999

(30) Foreign Application Priority Data

Dec. 1, 1998 (JP) ............................................ 10-341478
Nov. 19, 1999 (JP) ............................................ 11-329148

(51) Int. Cl.$^7$ ............................ A61F 13/15; A61F 15/20
(52) U.S. Cl. ................ 604/385.14; 604/604; 604/358; 604/368; 604/369; 604/572; 604/378; 604/385.1
(58) Field of Search ............................. 604/385.14, 358

(56) References Cited

U.S. PATENT DOCUMENTS

| 5,248,309 A | 9/1993 | Serbiak et al. |
| 5,591,150 A | 1/1997 | Olsen et al. |
| 5,609,588 A | 3/1997 | DiPalma et al. |
| 5,662,633 A * | 9/1997 | Doak .......................... 604/378 |

FOREIGN PATENT DOCUMENTS

EP 0 442 223 A1 8/1991

* cited by examiner

*Primary Examiner*—Andy Falik
*Assistant Examiner*—Angela J. Grayson
(74) *Attorney, Agent, or Firm*—Milbank, Tweed, Hadley & McCloy LLP

(57) ABSTRACT

An absorbent article including a laminated piece including a liquid-permeable top sheet, a back sheet and an absorbent core interposed between the top sheet and the back sheet. The region where the absorbent core is present includes a center region extending along a lengthwise direction of the absorbent article and side regions adjacent to the center region in a crosswise direction perpendicular to the lengthwise direction. The bending resistance (stiffness) of the laminated piece in the center region is higher than the bending resistance of the laminated piece in the side regions. The absorbent article can be attached in a stably fitting manner with no ready emergence of twisting or tucked-down wrinkles, when the absorbent article is overlaid on the inner face of an outer wear material.

20 Claims, 5 Drawing Sheets

ABSORBENT ARTICLE

FIELD OF THE INVENTION

The present invention relates to an absorbent article, for example urine-absorbing pad, pad against urine incontinence or sanitary napkin. More particularly, the present invention relates to an absorbent article capable of fitting in a stable manner with no occurrence of twisting or no emergence of tucked-down wrinkles, when used being overlaid on the inner face of an outer wear material, for example underwear or diaper.

BACKGROUND OF THE INVENTION

Absorbent articles such as urine-absorbing pad, pad against urine incontinence and sanitary napkin are generally used being overlaid on the inner face of an outer wear material such as underwear or diaper.

Such type of absorbent articles structurally comprises an absorbent core interposed between a liquid-permeable top sheet and a liquid-impermeable back sheet and sometimes additionally includes leg gatherings or vertical gatherings arranged on both sides thereof in the crosswise direction. These gathering are provided with elastic member materials such as rubber for providing a close fit to the legs or for standing up toward the skin of a wearer (user).

These conventional absorbent articles are prepared as soft as possible, taking account of the touch to the skin of a user. However, almost no attention has been paid to easy applicability or to the prevention of twisting or tucked-down wrinkles, which are significant when the absorbent article is used being overlaid on the inner face of an outer wear material such as underwear and diaper.

Particularly, regarding the one provided with the leg gatherings or vertical gatherings, because the elastic member materials for forming the leg gatherings or vertical gatherings are arranged in both sides of the absorbent article to extend. longitudinally at an elongated state, the resulting absorbent article readily deforms due to the shrinkage force of the elastic member materials, when the absorbent article is overlaid on an outer wear material. Consequently, the following drawbacks emerge.

1. It is difficult to attach the absorbent article along the inner face of an outer wear material such as underwear and diaper. In other words, it is difficult to attach the absorbent material in a relatively flat state to the inner face of an outer wear material such as underwear and diaper.
2. When attaching the absorbent article on the inner face of an outer wear material, the absorbent article readily twists or is tucked down and wrinkled; and moreover, during the motion of a body with the absorbent article attached thereon, the absorbent article twists or is tucked down and wrinkled or the degree of twisting or the number of tucked-down wrinkles is increased, so that body fluids readily leak from the side of the absorbent article.
3. It is difficult to attach the absorbent article on the very utmost bottom of an outer wear material. Particularly when the absorbent article is attached on the inner face of an underwear, because the absorbent article is inserted from the waist opening of the underwear into the inside of the underwear and then the legs are inserted into the underwear to wear the absorbent article together with the underwear, the absorbent article readily shifts in position or twists or is tucked down and wrinkled in the underwear until the underwear completely fits the body.

SUMMARY OF THE INVENTION

The present invention is solve the conventional problems as mentioned above, and an object of the invention is to provide an absorbent article capable of securely fitting human bodies with no ready occurrence of twisting or tucked-down wrinkles of the absorbent article when overlaid on the inner face of an outer wear material.

It is another object of the invention to provide an absorbent article which can be securely positioned and arranged at the central part of the lowest bottom of an outer wear material such as underwear.

The present invention provides an absorbent article comprising a laminated piece comprising a liquid-permeable top sheet, a back sheet and an absorbent core interposed between the top sheet and the back sheet, wherein the region where the absorbent core is present includes a center region extending along a lengthwise direction of the absorbent article and side regions adjacent to the center region in a crosswise direction perpendicular to the lengthwise direction, and the bending resistance (stiffness) of the laminated piece in the center region is higher than the bending resistance of the laminated piece in the side regions.

The absorbent article of the invention can be used as a urine-absorbing pad, a pad against urine incontinence, a sanitary napkin or the like, being overlaid on the inner face of an outer wear material such as underwear and diaper. By arranging the longitudinally extending center region with high bending resistance (stiffness) in the laminated piece composing the absorbent article, twisting or any tucked-down wrinkle hardly emerges in the absorbent article when the absorbent article is overlaid on the inner face of the outer wear material. Therefore, the absorbent article can be worn by a user in a stably fitting manner with no ready emergence of twisting or tucked-down wrinkles.

DETAILED DESCRIPTION OF THE INVENTION

Figure 1:
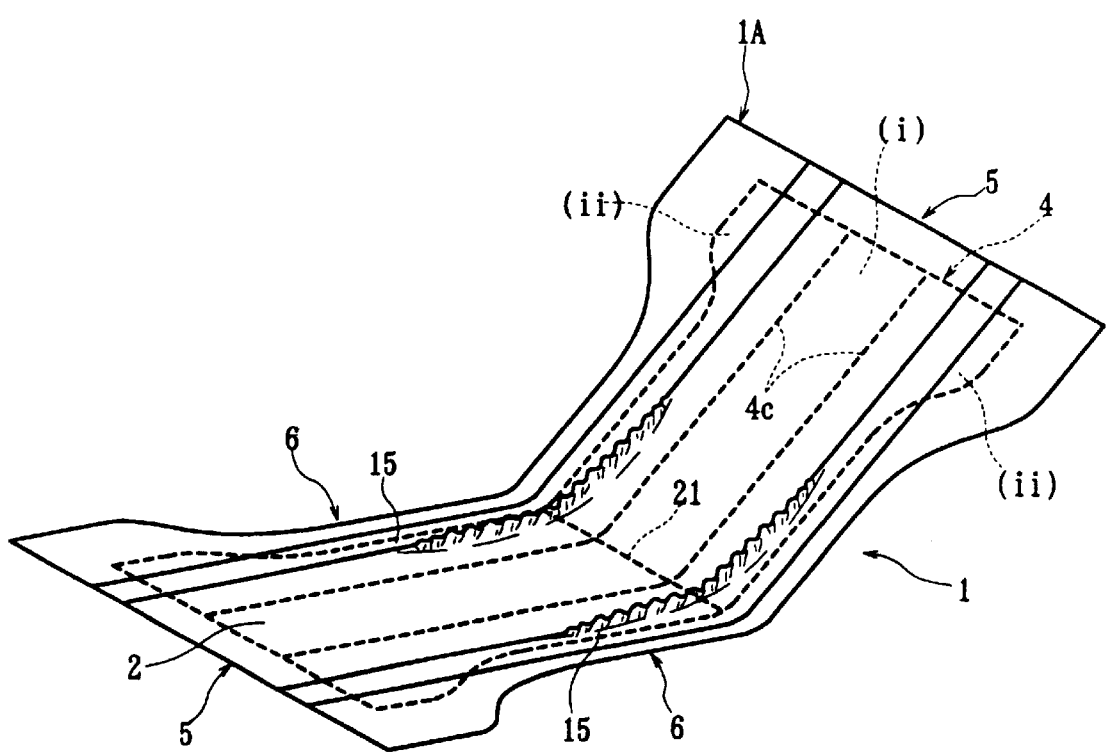
FIG. 1 is a perspective view of the absorbent article of the invention.
Figure 2:
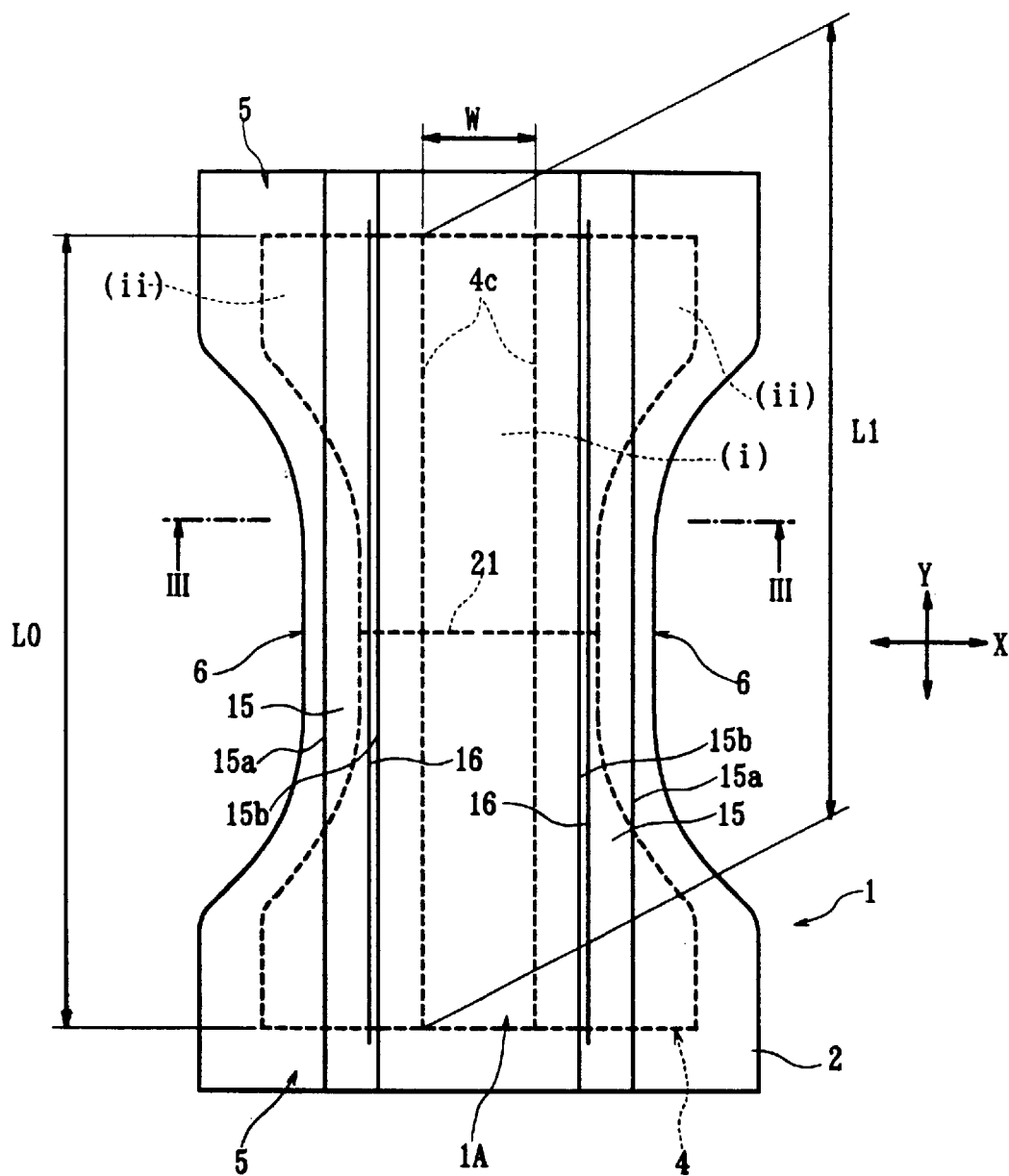
FIG. 2 is a plan view of the absorbent article shown in FIG. 1.
Figure 3:
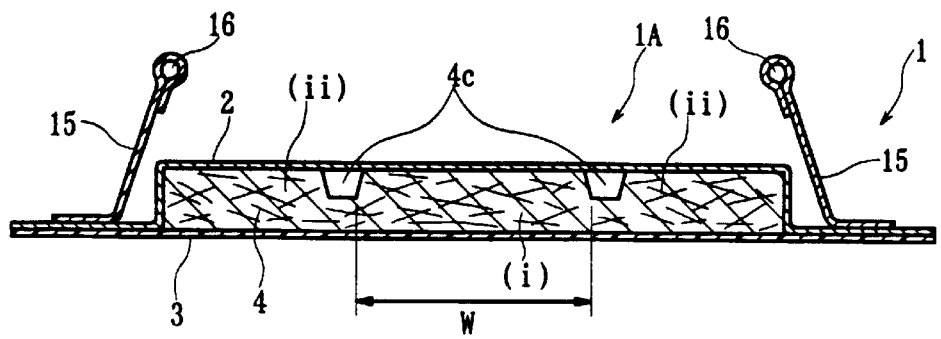
FIG. 3 is a cross-sectional view of FIG. 2 along the line III—III.
Figure 4:
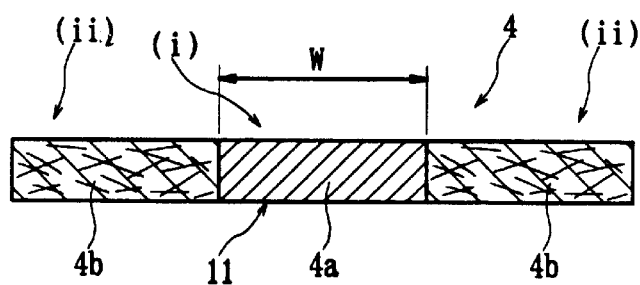
FIGS. 4(A), 4(B), and 4(C) are cross-sectional views of the structures of the bending resistance-enhancing means in the individual examples.
Figure 4:
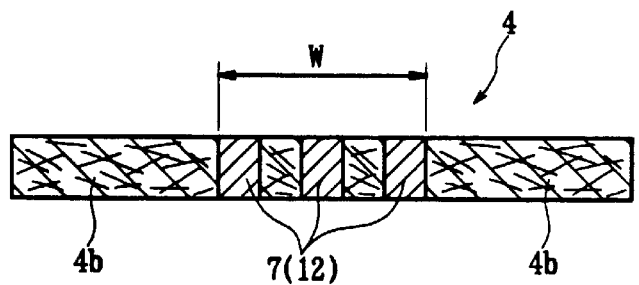
Figure 4:
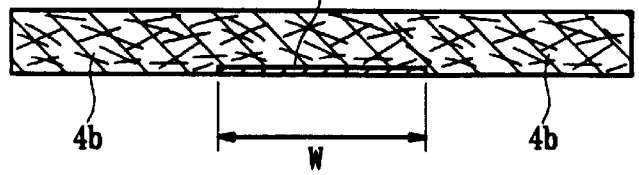
Figure 5:
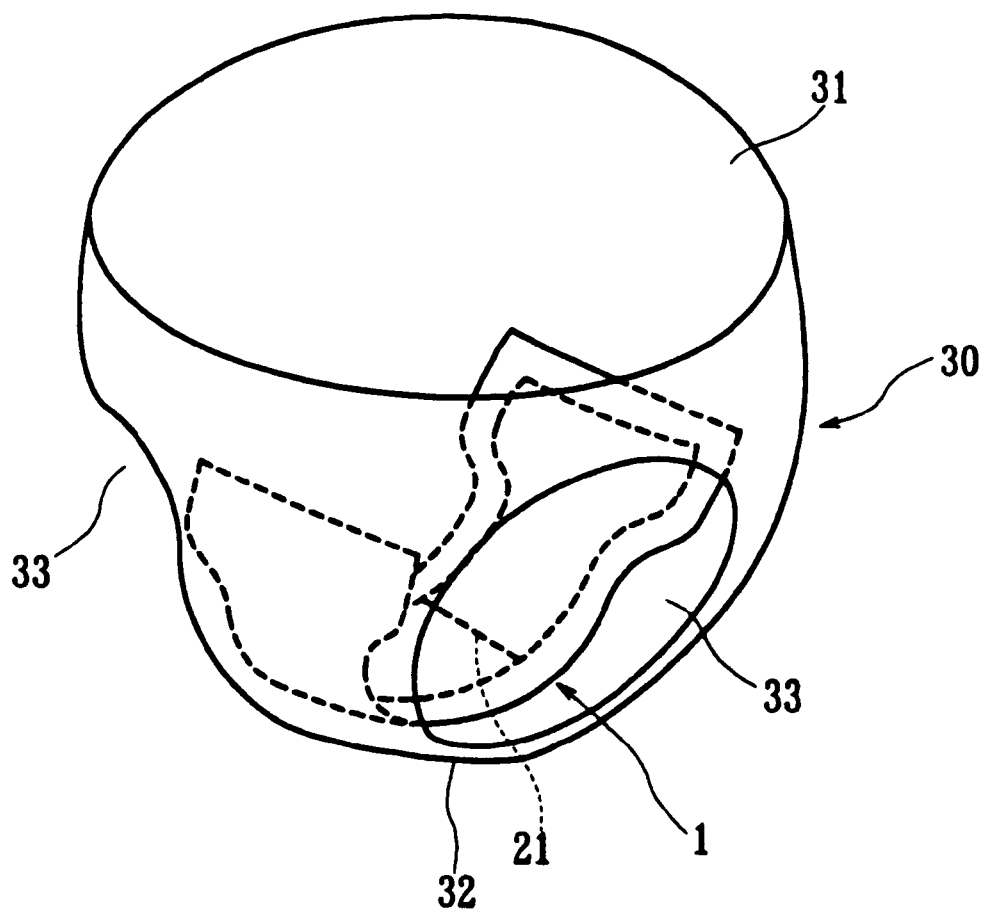
FIG. 5 is a perspective view depicting the attached state of the absorbent article to an outer wear material.

FIG. 1 is a perspective view of a urine-absorbing pad for adults (or a pad against urine incontinence) as one example of the absorbent article of the invention; FIG. 2 is a plan view showing the developed state thereof, FIG. 3 is a cross-sectional view of FIG. 2 along the line III—III; FIGS. 4(A), 4(B), and 4(C) are cross-sectional views of the structures of the bending resistance-enhancing means in the individual examples; and FIG. 5 is a perspective view depicting the state of the absorbent article attached to the inner face of an underwear as an outer wear material.

As shown in the cross-sectional view of FIG. 3, the absorbent article 1 comprises a laminated piece 1A composed of a liquid-permeable top sheet 2 facing toward the skin of a user, a back sheet 3 facing toward an outer wear material such as underwear and diaper, and an absorbent core 4 interposed between the top sheet 2 and the back sheet 3. The back sheet 3 can be a liquid-impermeable sheet. However, if the absorbent article 1 is to be arranged on the inner face of a diaper of pants type or open type as an outer wear material, a partial region or the whole region of the back sheet 3 may be prepared liquid permeable, so that urine remaining unabsorbed by the. absorbent core 4 of the absorbent article 1 can be transferable to the absorbent material of the diaper.

The liquid-permeable top sheet 2 is prepared by using hydrophilic fibers or hydrophilized hydrophobic fibers, and includes a non-woven fabric manufactured by point bond method, air through method, spun bond method, spun lace method or the like. The "hydrophilized hydrophobic fibers" as used herein means hydrophobic fibers subjected to hydrophilic treatment. In this hydrophilic treatment, a hydrophobic fiber is made hydrophilic by treating it with a surfactant; by chemically binding a chemical substance such as a monomer or a polymer having a hydrophilic group thereto; by subjecting it to plasma processing; by kneading it with a chemical substance having a hydrophilic group; or by treating its surface to have a profiled section. The back sheet 3 is made of an olefinic resin sheet, a non-woven fabric, a resin sheet overlaid on a nonwoven fabric or the like. The absorbent core 4 is prepared by using crushed pulp or a mixture of crushed pulp and super absorbent polymers (or highly absorbent polymers); and the absorbent core 4 comprises an absorbent sheet such as tissue, which wraps the crushed pulp or the mixture of crushed pulp and super absorbent polymers. The super. absorbent polymer (or SAP) can be made of polyacrylic acid, sodium polyacrylate, polyacrylamide, polyacrylonitrile, polyvinyl alcohol, an additional polymer of maleic anhydride, a polyether, a condensed polymer, a polysaccharide such as starch or cellulose, a protein such as collagen, or the like. Examples of the SAPs include: a cross-linked compound of sodium polyacrylate, a graft copolymer of starch having sodium polyacrylate or a graft copolymer of cellulose having polyacrylonitrile chains.

As shown in FIGS. 1 and 2, the top sheet 2 and the back sheet 3 while interposing the absorbent core 4 between them are overlaid together in terminal regions 5, 5 on both ends in the lengthwise direction of the absorbent article 1 and in terminal regions 6, 6 on both sides in the crosswise direction, where the two sheets 2 and 3 are bonded together with a hot-melt adhesive or the like.

In the absorbent article 1, the direction Y is a lengthwise direction, which extends from the lower abdominal region of a user toward the buttocks thereof in use, while the direction X perpendicular to the direction Y is a crosswise direction. The absorbent article 1 shown in FIGS. 1 and 2 is overall in a so-called sand glass shape, in which the top sheet 2, the back sheet 3 and the absorbent core 4 are all in so-called sand glass shapes. Herein, only the absorbent core 4 may be in a rectangular shape or the entirety of the absorbent article 1 may be in a rectangular shape.

Additionally, the absorbent article 1 is provided with hydrophobic sheets 15, 15 extending lengthwise adjacent to two sides of the narrow region of the sand glass shape. The side edge 15a of each hydrophobic sheet 15 is bonded to the inner face (or the top sheet 2) of the absorbent article 1, whereas the other side edge 15b thereof free from the top sheet 2 is provided with longitudinally extending elastic member material 16 (for example, rubber band) at its elongated state. As a result, as shown in FIG. 1, vertical gatherings for prevention of side leakage of urine or the like is formed on both sides of the absorbent article 1 standing up toward the skin of a user in use.

In the sand-glass shaped region where the absorbent core 4 is present as indicated by dotted line in FIG. 2, the center region (i) with given width W is made to have higher bending resistance (stiffness) than that of the remaining side regions (ii) adjacent to the center region (i) in the crosswise direction. In other words, the sand-glass shaped region where the absorbent core 4 is present has the center region (i) with high bending resistance and the side regions (ii) with low bending resistance.

Here in this specification, the "width" means the size in the crosswise direction and the "length" means the size in the lengthwise direction.

The difference in bending resistance can be established by arranging bending resistance-enhancing means in the center region (i).

The various examples of the bending resistance-enhancing means will be described with reference to the FIGS. 4(A) to 4(C).

First of all, in the absorbent article shown in FIG. 4(A), the bending resistance of the center region 4a of the absorbent core 4 (or the region within a range of the width W is made higher than the bending resistance of the side regions 4b, 4b of the absorbent core 4, and this center region 4a of the absorbent core 4 with high bending resistance composes bending resistance-enhancing means 11. Here, the region 4a corresponds to the region (i), and the regions 4b correspond to the regions (ii).

This can be achieved by making the fiber density in the center region 4a higher than the fiber density in the side regions 4b, 4b. For example, the absorbent core 4 may be formed such that: the center region 4a and the side regions 4b, 4b are formed of a fiber layer at a constant thickness; another fiber layer is overlaid only on the center region 4a; and then only the center region 4a or all the center region 4a and the side regions 4b, 4b are pressurized or heated under pressure to make the whole absorbent core 4 at the same thickness. Alternatively, during the course of forming the absorbent core 4, a fiber web may be prepared to have larger bulkiness (or larger METSUKE) in the center region 4a and to have smaller bulkiness (or smaller METSUKE) in the side regions 4b, 4b, and then pressurized or heated under pressure, to make a fiber layer at the same thickness. In such manner, the bending resistance of the center region 4a can be increased more than the bending resistance of the side regions 4b, 4b.

Otherwise, the bending resistance of the center region 4a can be elevated more than the bending resistance of the side regions 4b, 4b such that thermoplastic fibers after hydrophilic treatment are contained more in the center region 4a of the absorbent core 4 than in the side regions 4b, 4b; by subsequently blowing hot air over the center region 4a or the whole absorbent core 4 thereby thermally melting together thermoplastic fibers in the center region 4a relatively more than in the side regions 4b, 4b. In such manner, the center region 4a per se of the absorbent core 4 is allowed to function as the bending resistance-enhancing means 11.

Otherwise, when the absorbent core 4 comprises a mixture of absorbent fibers such as crushed pulp and/or hydrophilic fibers (including hydrophilized hydrophobic fibers) and a highly absorbent polymer, the bending resistance of the center region 4a can be sufficiently elevated such that the amount of the highly absorbent polymer contained in the center region 4a is increased more than the amount of the highly absorbent polymer contained in the side regions 4b, 4b; or the highly absorbent polymer is contained only in the center region 4a; by subsequently adding a small quantity of water to the absorbent core 4, thereby making the fibers adhere together through the highly absorbent polymer.

In FIG. 4(B), reinforcing member material 7 is embedded in the absorbent core 4 within the region (i) of the width W. The reinforcing member material 7 serves as bending resistance-enhancing means 12.

In the side regions with no reinforcing member material arranged therein, the absorbent core 4 comprises absorbent material such as absorbent fibers or a mixture of absorbent fibers with a highly absorbent polymer. The reinforcing member material 7 comprises, for example, an air through non-woven fabric with high rigidity, as prepared by thermally melting thermoplastic fibers after hydrophilic treatment. In order to avoid the reduction of the water absorptivity and retentivity of the absorbent core 4 in the region (i) of the width W, preferably, the absorbent material and the reinforcing member material 7 are alternately arranged in the region (i) of the width W in the crosswise direction, as shown in FIG. 4(B). More preferably, the reinforcing member material 7 is embedded in a striped pattern continuously extending longitudinally.

The reinforcing member material 7 thus arranged can elevate the bending resistance of the region (i) of the width W more than the bending resistance of the side regions 4b, 4b adjacent thereto.

In FIG. 4(C), reinforcing member material 8 is arranged according to the region (i) of the width W. The reinforcing member material 8 serves as bending resistanceenhancing means 13.

The reinforcing member material 8 is a reinforcing plate of a relatively small thickness, a large length, and the width W. The reinforcing plate comprises cardboard, resin sheet, foaming resin plate or the like. The reinforcing plate may satisfactorily be embedded in the absorbent core 4 or may satisfactorily be interposed between the absorbent core 4 and the back sheet 3. In this case, the reinforcing plate may satisfactorily be bonded to the absorbent core 4 or may satisfactorily be bonded to the back sheet 3. Alternatively, the reinforcing plate may satisfactorily be bonded to the exterior face of the back sheet 3. Still additionally, plural reinforcing plates may be satisfactorily used and arranged at an interval within the region of the width W in the crosswise direction.

In the embodiment of the FIGS. 1 and 2, the region (i) with high bending resistance is in a rectangle shape of the constant width W. However, the region (i) may satisfactorily be in a sand glass shape or the like.

As shown in FIG. 3, furthermore, grooves 4c extending longitudinally are preferably formed in the absorbent core 4, along the borders between the high bending resistance region (i) and the low bending resistance regions (ii). The grooves 4c are omitted in the cross-sectional views of FIGS. 4(A) to 4(C). In order to form the groove 4c, the absorbent core 4 is compressed and thinned (e.g., by embossing roll) or the fibers composing the absorbent core 4 are removed. The groove 4c thus arranged permits free deformation of the absorbent core 4 in the low bending resistance regions (ii) under no influence of the high bending resistance region (i).

In the center of the absorbent article 1 in the lengthwise direction, a folding part (folding line) 21 extending along the crosswise direction is preferably formed, as shown in FIGS. 1 and 2. In this case, the bending resistance of the region (i) is relatively lowered at the folding part 21. This can be attained by creasing the center region 4a of the absorbent core 4, the reinforcing member material 7 or the reinforcing member material 8, respectively composing the bending resistance-enhancing means 11, 12 or 13, along the folding part 21, or by partially removing the reinforcing member materials and the like along the folding part 21. Incidentally, this folding part 21 may be formed to extend across not only the region (i) but also the regions (ii), i.e., across the whole absorbent core 4.

In this case, the absorbent article 1 can be readily folded at the folding part 21 and packaged at a double-folded state. Otherwise, the folding part 21 can be arranged at two positions at an interval in the lengthwise direction, so that the absorbent article 1 can be triple-folded.

Because the laminated piece 1A composing the absorbent article 1 has the high bending resistance region (i) thus described, the absorbent article 1 can readily maintain its relatively flat state during use. On the other hand, by folding the absorbent article 1 along the folding part 21, the absorbent article 1 can be packaged compactly.

FIG. 5 depicts one example of the state of the absorbent article 1 during use. Symbol 30 represents underwear (or diaper of pants type) as an outer wear material.

Upon use, the absorbent article 1 is spread as shown in FIG. 1, and is then inserted from the waist opening 31 of the underwear 30 to be attached to the bottom part 32 (or crotch region) of the underwear 30, as shown in FIG. 5. Here, the absorbent article 1 can be securely positioned at the center of the bottom part 32 of the underwear 30, by attaching the absorbent article 1 with its folding part 21 in accord with the center of the bottom part 32 of the underwear 30.

While the absorbent article 1 is attached to the inside of the underwear 30, the underwear 30 is worn such that the legs of a user are inserted from the waist opening 31 into the leg openings 33. In this wearing process, because the high bending resistance region (i) functions to maintain the flat state, the absorbent article 1 is never twisted or is never tucked down or wrinkled inside the underwear 30. Additionally, because the folding part 21 works as a marker to apply the absorbent article 1 at the center of the bottom part 32 of the underwear 30, the absorbent article 1 never shifts severely in position during wearing.

Moreover, while the absorbent article 1 is applied to the crotch region of a user, the high bending resistance region (i) works to maintain the absorbent article 1 per se at the flat state. Thus, no twisting or no tucked-down wrinkle emerges in the absorbent article 1 during wearing. Because the low bending resistance regions (ii) are present outside the region (i), additionally, the regions (ii) can freely deform conforming to the shape from the crotch region of a user to the thigh thereof so that the absorbent article 1 can securely fit the crotch region.

Because the regions (ii) are flexible, the deformation of the regions (ii) readily allows the hydrophobic sheets 15 to stand up toward the skin of a user, so that the vertical gatherings are readily formed on both sides in the crosswise direction, which works to prevent urine leakage from the side.

Particularly when the grooves 4c, 4c extending longitudinally are formed in the absorbent core 4, along the borders between the high bending resistance region (i) and the low bending resistance region (ii), the region (i) can be separated from the region (ii), whereby the region (ii) can freely deform under not so severe influence of the bending resistance of the region (i).

In order to permit the region (ii) freely deformable, the bending resistance of the laminated piece in the region (ii) in the lengthwise direction (direction Y) as measured before use (i.e., when no liquid is absorbed) at a Taber stiffness test according to JIS P8125 is preferably 19 mN·cm or more to 400 mN·cm or less. Here, "the bending resistance of the laminated piece in the region (ii)" means the bending resistance of the absorbent core in the region (ii) along with the top sheet and the back sheet. Within this range, the absorbent core 4 in the region (ii) can keep gentle touch on skin. More preferably, it is 19 mN·cm or more to 200 mN·cm or less. The most preferably, it is 19.6133 mN·cm or more to 196.133 mN·cm or less.

For adults, the width (or maximum size in the direction X) of the absorbent core 4 is about 100 mm; and the width W of the high bending resistance region (i) is 10 mm or more to 60 mm or less, preferably. When the width W is above 60 mm, the region (i) extends nearly up to the thigh of an adult, so that the adult might readily feel uncomfortable at the crotch region while wearing the absorbent article 1. When the width W is below 10 mm, the area of the low bending resistance region (ii) is enlarged, which readily causes the absorbent article 1 to be tucked down on both the sides in the crosswise direction and deteriorates the fitting stability on the body. Taking account of what has been described above, the width W of the high bending resistance region (i) is more preferably 15 mm or more to 20 mm or less.

Incidentally, if the region (i) is in a sand glass shape or the like with no constant width, the width of the region (i) in the center of the absorbent article in the lengthwise direction should be taken as the width W.

Furthermore, it is preferable that: the bending resistance of the laminated piece in the region (i) in the lengthwise direction is 2-fold or more the bending resistance of the laminated piece in the region (ii) in the lengthwise direction, as measured at a Taber stiffness test according to JIS P8125, before use (i.e., when no liquid is absorbed); and the bending resistance of the laminated piece in the region (i) in the lengthwise direction is equal to or more than the bending resistance of the laminated piece in the region (ii) in the lengthwise direction, as measured at the same test, after absorption of liquid. Here, "the bending resistance of the laminated piece in the region (i)" means the bending resistance of the absorbent core (including the bending resistance-enhancing means) in the region (i) along with the top sheet and the back sheet. As has been described above, in the laminated piece in the region (i), there is provided the bending resistance-enhancing means 11, 12 or 13. The bending resistance-enhancing means 11, 12 and 13 comprise the center region 4a of the absorbent core 4 where the bending resistance is enhanced, the reinforcing member material 7 such as rigid non-woven fabric and the reinforcing member material 8 such as cardboard, respectively.

By allowing the laminated piece in the region (i) (or in the region including the bending resistance-enhancing means 11, 12 or 13) to have the bending resistance of 2-fold or more the bending resistance of the laminated piece in the region (ii) as described above, the flatness degree of the absorbent article 1 when applied to a user can be increased, which works to prevent the occurrence of twisting or tucked-down wrinkles.

Still furthermore, the high bending resistance region (i) is required to be present at least in the center of the absorbent article 1 in the lengthwise direction. In other words, the region (i) is required to include the centerline extending along the crosswise direction. Additionally, under provision that the length of the region (i) is designated as L1 and the length of the absorbent core 4 is designated as L0, preferably, the length L1 corresponds to ½-fold or more of the length L0. In such configuration, the twisting of the absorbent article 1 or the emergence of tucked-down wrinkles in the absorbent article 1 can be prevented at least in the region to be applied to the crotch region of a user.

The absorbent article of the present invention is not limited to the use thereof in the inner face of underwear or diaper of pants type. The absorbent article can be attached to the inner face of diaper of open type for use. The absorbent article may satisfactorily be used as sanitary napkin.

Figure 6:
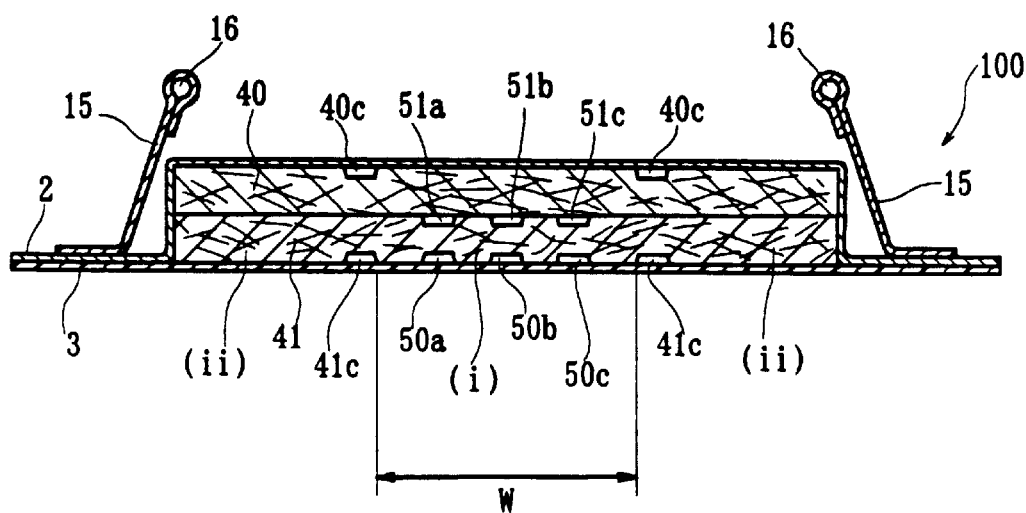
FIG. 6 is a cross-sectional view showing a still another embodiment of the absorbent article according to the invention.

FIG. 6 is a cross-sectional view showing a still another embodiment of the absorbent article according to the invention.

The absorbent article 100 shown in FIG. 6 has substantially the same constructions as the absorbent article 1 shown in FIGS. 1 and 2, except for the absorbent core and bending resistance-enhancing means. Therefore, the detailed description of the portions having the same constructions will be omitted by designating them by the common reference numerals.

In the absorbent article 100 shown in FIG. 6, the absorbent core is in a two-layer structure of an upper layer 40 and a lower layer 41. The upper layer 40 and the lower layer 41 are respectively formed of the same materials of the absorbent core 4 as mentioned above. That is, the upper layer 40 and the lower layer 41 are respectively prepared by using crushed pulp or a mixture of crushed pulp and super absorbent polymers (or highly absorbent polymers). The crushed pulp or the mixture of crushed pulp and highly absorbent polymers is wrapped in an absorbent sheet such as tissue.

In this case, it is preferable that the upper layer 40 is formed only of crushed pulp and the lower layer 41 is formed of the a mixture of crushed pulp and highly absorbent polymers, so that the excretory liquid such as urine can be readily transferred from the upper layer 40 into the lower layer 41. In this case, moreover, the upper layer 40 and the lower layer 41 may be wrapped in the absorbent sheets respectively, or the upper layer 40 and the lower layer 41 may be wrapped in the absorbent sheet together. Still moreover, the upper layer 40 may be formed only of hydrophilized hydrophobic fibers to function as a liquid-permeable cushion layer, so that the excretory fluid given to the upper layer 40 is not so maintained with the upper layer 40 but can readily permeate into the lower layer 41.

The center region of the lower layer 41 as indicated by the width W1 (hereinafter referred to as "center region W1") is provided with bending resistanceenhancing means. In this embodiment, a plurality of recesses extending continuously along the lengthwise direction of the absorbent article 100 are formed on both faces of the lower layer 41 by compressing the lower layer 41. The recesses 50a, 50b and 50c are formed on the lower face of the lower layer 41, and the recesses 51a, 51b and 51c, corresponding the recesses 50a, 50b and 50c respectively, are formed on the upper face of the lower layer 41. With these recesses formed, the fiber density of the compressed portions therebetween (or thin portions of the lower layer 41 due to the recesses) is increased, so that the bending resistance of the center region W1 is enhanced. These recesses can be formed by using an embossing roll or an embossing plate. Moreover, in order to form the recesses more securely, the embossing treatment is preferably performed under heating. For example, the recesses can be formed by using a heat embossing roll.

In the lower layer 41, the bending resistance of the center region W1 is higher than (preferably 2-fold or more) the bending resistance of the remaining side regions.

On the upper side (the side facing the wearer) of the lower layer 41, there is placed the upper layer-40. The center region of the upper layer 40 has no recess unlike the lower layer 41. Therefore, the bending resistance of the upper layer 40 in the portions to be placed on the center region W1 is lower than the bending resistance of the lower layer 41 in the center region W1. Due to the presence of this upper layer 40, the wearer feels no stiffness of the lower layer 41, so that the absorbent article 100 can provide a soft touch. As has been described above, the absorbent core where the upper and lower layers 40, 41 are laminated is provided with the center region (i) with high bending resistance and the side regions (ii) with low bending resistance.

Additionally, in the aforementioned absorbent core, there are formed grooves 40c, 41c extending longitudinally, at the borders between the center region (i) and the side regions (ii). The grooves 40c are formed on the upper face of the upper layer 40, whereas the grooves 41c are formed on the lower face of the lower layer 41. These grooves 40c, 41c are formed by compressing the fibers composing the absorbent core, like the recesses for the bending resistance-enhancing means. In the production process thereof it is preferable that the upper layer 40 and the lower layer 41 should be laminated before compressing step for forming the grooves, so that the grooves 40c are in exact overlying relation with the grooves 41c. For compressing, an embossing roll, an embossing plate, a heat embossing roll or the like can be employed.

With these grooves 40c, 41c provided, the side regions of the lower layer 41 can freely deform under no influence of the high bending resistance of the center region W1 of the lower layer 41. Further, the upper layer 40 can be readily folded at the borders between the center region and the side regions. Therefore, the side regions of the upper layer 40 can readily deform along with the side regions of the lower layer 41, so that the absorbent article 100 as a whole can closely fit the shape of crotch region and can correspond to the change of posture of the body.

Here, because the recesses and the grooves are formed by compressing the absorbent core, the fiber density of the compressed portions is increased. Therefore, the rate of absorption of the excretory liquid is accelerated in the vicinity of the recesses and the grooves due to the capillary phenomenon. Moreover, the absorptivity is also enhanced because the excretory liquid is readily dispersed in the lengthwise direction through the recesses and the grooves.

In the above embodiment, the recesses for forming the bending resistanceenhancing means (i.e., the compressed portions) are described to extend linearly and continuously in the lengthwise direction, but they can be arranged in any shape such as intermittent line or corrugated line or a pattern such as circle, square, triangle or the like. Further, the lower layer 41 may be compressed all over the center region W1 to form the bending resistance-enhancing means. In addition, the absorbent core may be constructed by laminating three or more layers. When the absorbent core is constructed in a multi-layer structure, moreover, the recesses for forming the bending resistance-enhancing means may also be formed on the center region of an uppermost layer (top layer) for facing the wearer. In this case, however, the total area of the recesses formed on the top layer is preferably smaller than that of the recesses formed on a layer lower than the top layer so that the absorbent article is comfortable to wear. Here, needless to say, it is also possible that the lower layer 41 having the bending resistance enhanced region is prepared according to the examples shown in FIGS. 4(A) 4(B) and 4(C). In other words, another absorbent core layer may be arranged on the absorbent core of FIG. 4(A), 4(B) or 4(C), so that the absorbent article is comfortable to wear. As has been described above, the absorbent article of the present invention can prevent the occurrence of twisting or tucked-down wrinkles during wearing; additionally, the absorbent article of the present invention closely fits the crotch region of a user, with no deterioration of good wearing touch or feeling. Moreover, the absorbent article of the present invention can readily be attached to outer wear materials such as underwear. Still moreover, when the absorbent core is in a two-layer structure as shown in FIG. 6, the absorbent article can provide comfortable touch at the center region of the absorbent core, even though the bending resistance-enhancing means is provided thereto.

In the foregoing specification, the invention has been described in relation to preferred embodiments and many details have been set forth for the purpose of illustration. It will be apparent to those skilled in the art that the invention is susceptible to additional embodiments and that certain of the details described herein can be varied considerably without departing from the basic principles of the invention.

Further, 'comprises/comprising' when used in this specification is taken to specify the presence of stated features, integers, steps or components but does not preclude the presence or addition of one or more other features, integers, steps, components or groups thereof.

What is claimed is:

1. An absorbent article comprising a laminated piece comprising a liquid-permeable top sheet, a back sheet and an absorbent core interposed between the top sheet and the back sheet,
   wherein the region where the absorbent core is present includes a center region extending along a lengthwise direction of the absorbent article and side regions adjacent to the center region in a crosswise direction perpendicular to the lengthwise direction, and the bending resistance of the laminated piece in the center region is higher than the bending resistance of the laminated piece in the side regions,
   wherein grooves are formed in the absorbent core to extend along the borders between the center region and the side regions.

2. An absorbent article according to claim 1, wherein the width of the center region is 10 mm to 60 mm, at least in the center of the absorbent core in a lengthwise direction.

3. An absorbent article according to claim 1, wherein the length of the center region is at least half the length of the absorbent core.

4. An absorbent article according to claim 1, wherein at least the center region is partially softened to form a folding part extending in a crosswise direction.

5. An absorbent article according to claim 1, wherein the center region of the absorbent core contains thermoplastic fibers treated to be hydrophilic in a greater amount than the side regions, and the thermoplastic fibers are thermally melted to each other so that the bending resistance of the absorbent core in the center region is higher than the bending resistance of the absorbent core in the side regions.

6. An absorbent article according to claim 1, wherein the absorbent core contains highly absorbent polymer in the center region only or in a greater amount than in the side regions, and fibers forming the absorbent core are adhered to each other through the highly absorbent polymer so that the bending resistance of the absorbent core in the center region is higher than the bending resistance of the absorbent core in the side regions.

7. An absorbent article according to claim 1, wherein reinforcing members for enhancing the bending resistance are embedded in the absorbent core to be located within the center region so that the reinforce member and the absorbent core alternate with each other in a crosswise direction.

8. An absorbent article according to claim 1, wherein a reinforcing plate for enhancing the bending resistance is disposed between the absorbent core and the back sheet to be located within the center region.

9. An absorbent article according to claim 1, wherein the absorbent core is provided with a plurality of recesses, which extend in the lengthwise direction and are located within the center region, the recesses being formed by pressurizing the absorbent core to enhance the bending resistance of the absorbent core in the center region.

10. An absorbent article according to claim 9, wherein the absorbent core comprises an upper layer and a lower layer underlying the upper layer, and the recesses are formed in the lower layer only.

11. An absorbent article comprising a laminated piece comprising a liquid-permeable top sheet, a back sheet and an absorbent core interposed between the top sheet and the back sheet, wherein the region where the absorbent core is present includes a center region extending along a lengthwise direction of the absorbent article and side regions adjacent to the center region in a crosswise direction perpendicular to the lengthwise direction, and the bending resistance of the laminated piece in the center region is higher than the bending resistance of the laminated piece in the side regions, wherein the center region of the absorbent core is partially pressurized to have a plurality of recesses extending in a lengthwise direction so that the bending resistance of the absorbent core in the center region is higher than that in the side regions.

12. An absorbent article according to claim 11, wherein the absorbent core comprises an upper layer and a lower layer underlying the upper layer, and the recesses are formed in the lower layer only.

13. An absorbent article according to claim 12, wherein grooves are formed in the upper layer to extend along the borders located between the center region and the side regions and extending in a lengthwise direction.

14. An absorbent article according to claim 13, wherein other grooves are formed in the lower layer to underlie the grooves formed in the upper layer.

15. An absorbent article according to claim 11, wherein the width of the center region is 10 mm to 60 mm, at least in the center of the absorbent core in a lengthwise direction.

16. An absorbent article according to claim 11, wherein the length of the center region is at least half the length of the absorbent core.

17. An absorbent article according to claim 11, wherein at least the center region is partially softened to form a folding part extending in a crosswise direction.

18. An absorbent article according to claim 11, wherein when the absorbent article is not in a fluid absorption state, the lengthwise bending resistance of the laminated piece in the center region is at least twice the lengthwise bending resistance of the laminated piece in the side regions, as measured at Taber stiffness test according to JIS P8125.

19. An absorbent article according to claim 18, wherein when the absorbent article is in a fluid absorption state, the lengthwise bending resistance of the laminated piece in the center region is equal to or more than the lengthwise bending resistance of the laminated piece in the side regions, as measured at Taber stiffness test according to JIS P8125.

20. An absorbent article according to claim 18, wherein when the absorbent article is not in a fluid absorption state, the lengthwise bending resistance of the laminated piece in the side regions is 19 mN·cm to 400 mN·cm, as measured at Taber stiffness test according to JIS P8125.

\* \* \* \* \*

UNITED STATES PATENT AND TRADEMARK OFFICE
CERTIFICATE OF CORRECTION

PATENT NO.    : 6,423,046 B1
DATED         : July 23, 2002
INVENTOR(S)   : Fujioka et al.

It is certified that error appears in the above-identified patent and that said Letters Patent is hereby corrected as shown below:

<u>Title page,</u>
Item [73], should read as follows:
-- [73]    Assignee: Uni-Charm Corporation, Ehime [JP] --.

Signed and Sealed this

Sixth Day of May, 2003

JAMES E. ROGAN
*Director of the United States Patent and Trademark Office*